United States Patent [19]

Ezis et al.

[11] Patent Number: 4,632,793
[45] Date of Patent: Dec. 30, 1986

[54] METHOD OF FABRICATING HOT PRESSED SILICON NITRIDE BILLETS

[75] Inventors: Andre Ezis, Grosse Ile; Elaine C. Beckwith, Riverview; Warren B. Copple, Dearborn Heights, all of Mich.

[73] Assignee: Ford Motor Company, Dearborn, Mich.

[21] Appl. No.: 848,845

[22] Filed: Apr. 3, 1986

Related U.S. Application Data

[63] Continuation of Ser. No. 635,943, filed as PCT US82/01369, Sep. 30, 1982, § 102(e) date Sep. 30, 1982, abandoned, which is a continuation-in-part of Ser. No. 444,246, Sep. 30, 1982, abandoned.

[51] Int. Cl.⁴ .......................................... C04B 35/58
[52] U.S. Cl. .................................. 264/58; 264/325; 264/332
[58] Field of Search ..................... 264/58, 325, 332

[56] References Cited

U.S. PATENT DOCUMENTS

| | | | |
|---|---|---|---|
| 3,264,388 | 8/1966 | Rouch | 264/332 |
| 3,535,132 | 10/1970 | Lunde | 264/332 |
| 3,632,708 | 1/1972 | Mandorf et al. | 264/332 |
| 4,096,120 | 6/1978 | Grunke | 264/332 |
| 4,172,107 | 10/1979 | Nakamura et al. | 264/332 |
| 4,315,876 | 2/1982 | Baker et al. | 264/332 |
| 4,477,402 | 10/1984 | Ezis | 264/332 |
| 4,489,032 | 12/1984 | Ezis et al. | 264/332 |
| 4,508,671 | 4/1982 | Ezis | 264/58 |

FOREIGN PATENT DOCUMENTS 1405171  9/1975  United Kingdom .

OTHER PUBLICATIONS

Alper, "High Temperature Oxides," Refractory-Materials, vol. 5, III, 1970, pp. 184-189.

Primary Examiner—James Derrington
Attorney, Agent, or Firm—Leonard Tachner

[57] ABSTRACT

A method is disclosed of making a plurality of dimensionally accurate hot pressed ceramic bodies. A plurality of $Si_3N_4$ plates having a thickness to width ratio of 1:3 to 1:40 are stacked in a hot pressing assembly (40-41-42-43). The plates are arranged in groups of progressively decreasing number so that (a) for a plate group (10-11-12-13-14) residing in a zone of compression (15) that will experience the least movement along the pressing direction the stacked number of plates is greatest within such group, and (b) for a plate group residing in a zone of compression (22) that will experience the most movement along the pressure direction the stacked number of plates (21) within such group is the lowest, each group being separated from adjacent groups by an inert rigid spacer.

11 Claims, 3 Drawing Figures

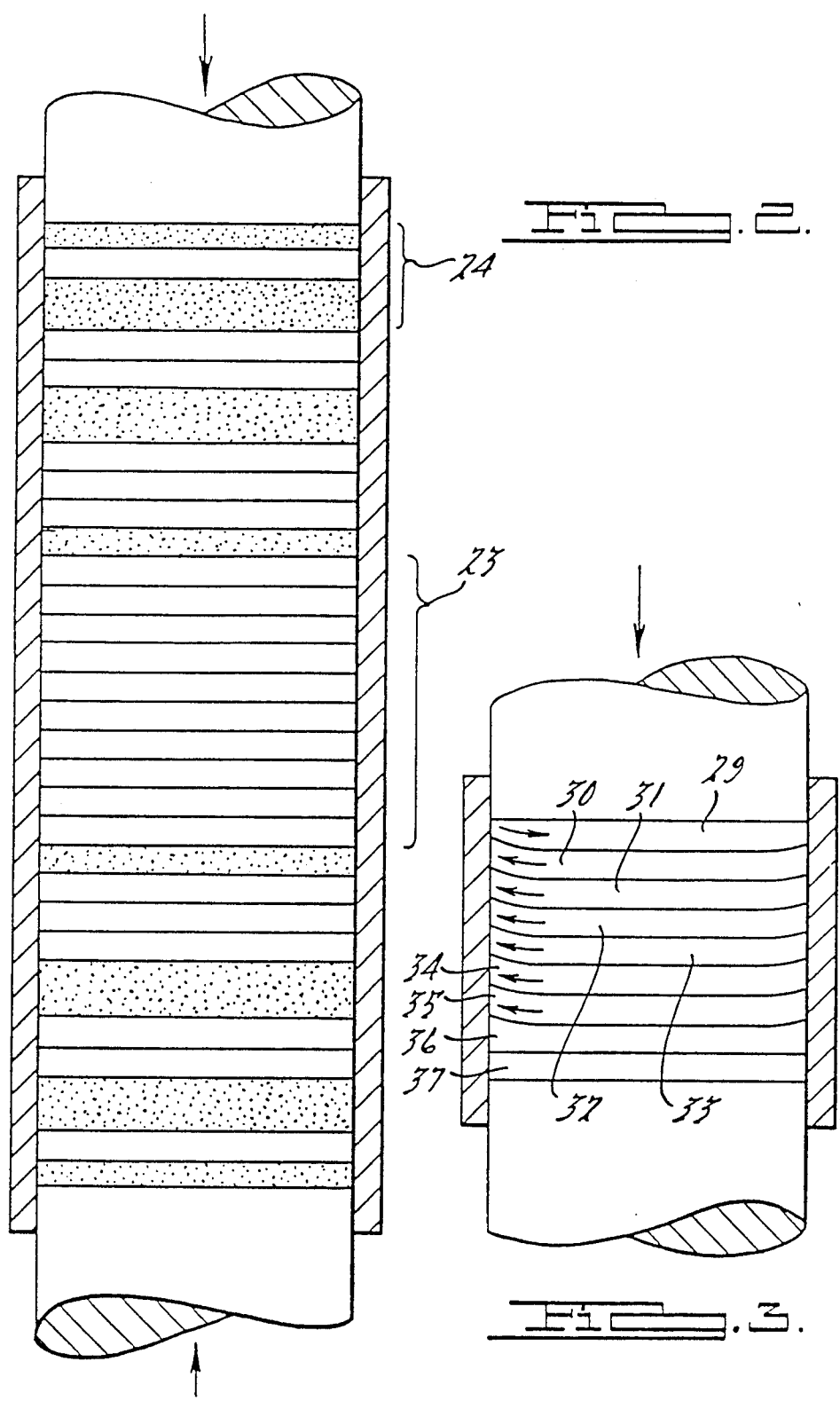

METHOD OF FABRICATING HOT PRESSED SILICON NITRIDE BILLETS

RELATED APPLICATION

This application is a continuation of application Ser. No. 635,943, filed a PCT US82/01369, Sept. 30, 1982, § 102(e) date Sept. 30, 1986, now abandoned which is a continuation in part of U.S. Ser. No. 444,246, filed Sept. 30, 1982 now abandoned.

BACKGROUND AND PRIOR ART STATEMENT

The present invention is directed to a method of making a more economical and distortion-free silicon nitride product suitable for use as one or more cutting tools by hot pressing with significantly reduced need for subsequent shaping.

Hot pressing of ceramic starting materials has been known for some time (see Refractory-Materials, Alper, Vol. 5, III, "High Temperature Oxides", 1970, pp. 184–189, for an explanation of the typical hot pressing process and equipment). The hot pressing sequence usually involves placing a loose particulate powder mixture or semidense pressed block of the powder mixture into a pressing assembly and heating the assembly while applying pressure to the mass sufficient to densify and fuse the particles to a desired degree. Typically, the pressing assembly is a cylindrical die closed by end plungers or pistons, one or both of such end plungers or pistons being forceably moved by platens of a press to apply pressure to the mass within the assembly. The cylinder and end plungers are close fitting and are typically constructed of graphite. A refractory insulation shell is wrapped about the cylindrical die assembly and heat is applied thereto by induction coils or by resistance heating. For making a silicon nitride comprising ceramic, hot pressing is typically carried out in the temperature range of 1500°–1850° C., the pressures employed usually are in the range of 2000–7000 psi, and the time period usually comprises 5–180 minutes. The resulting density for silicon nitride so hot pressed is usually in the range of 3.15–3.40 gm/cm$^3$.

The conventional hot pressing technique has not achieved a desirable level of productivity and economy. At best, such art has attempted to simultaneously hot press a plurality of aligned loose powder volumes, each volume separated from the other by a fully dense, thick and rigid spacer effective to transmit pressure forces like a wall of the pressure assembly. Each such spacer limited the capacity of the assembly to increase productivity and in many cases occupied more space than the bodies to be pressed (see U.S. Pat. Nos. 3,535,132; 3,632,708; and 3,264,388).

In the interest of economy and productivity, if the hot pressing sequence were to be employed for the simultaneous pressing of a plurality of stacked, cold compacted, flat ceramic plates (particularly large diameter plates on the order of a 6 inch diameter or greater), several problems would be encountered. First, a temperature gradient is created across the lateral width of the plates which results in a corresponding viscosity gradient. Such viscosity gradient causes the pressing assembly to apply a nonuniform pressure distribution across and through the mass of the plates. Secondly, there exists a drag force (a friction force between the pressing assembly walls and the plate sides) which also contributes to a nonuniform pressure distribution across the lateral width of the plates. These two factors together cause material transport under the hot pressing conditions which in turn results in "dishing" or severe distortion of the flat plates in their fully densified condition. Lacking dimensional accuracy such hot pressed bodies would require expensive reconditioning to redefine for use.

In only one instance has the prior art attempted to simultaneously hot press a plurality of silicon nitride components. In British Pat. No. 1,405,171, a number of cold compacted preforms are placed in a single layer within a pressing assembly, each preform having a thickness generally equal to its width. Each preform is separated from all others by a release agent. No greater than two layers are used. The problems overcome by this invention would not be experienced in the application of this British patent. Side wall drag would be insufficient to promote distortion since there is little difference in movement between layers; the preforms do not contact the die wall and the thickness to width ratio is only 1:1. Material transport cannot take place as a result of pressure and thermal gradients because there is little relative movement between layers, little or no side wall drag, and the thickness to width ratio is only 1:1. The disclosure thus fails to appreciate the need for a unique stacking sequence that would eliminate dishing in the hot pressing of multiples of billets having a thickness to width ratio of 1:3–1:40.

SUMMARY OF THE INVENTION

The invention is a method of substantially reducing dishing in the simultaneous hot pressing of a multiple number of stacked, predensified ceramic plates. The method comprises: (a) preparing a plurality of ceramic plates having a thickness to width ratio in the range of 1:3 to 1:40 and a density in the range of 50–80% of theoretical; (b) uniquely stacking a multiple number of said plates directly on top of one another within groups and placing said groups into a pressure assembly in such a manner as to be aligned with a common wall effective to support said plates normal to the direction of pressure to be applied; and (c) hot pressing the stacked groups of plates under pressure and temperature to densify each of said plates to at least 95% of theoretical density with a compression ratio of 1.2:1 to 2:1. The unique stacking is in groups of progressively decreasing number so that for a plate group residing in a zone of compression that will experience the least movement along the pressing direction, the stacked number of plates is greatest within such group. For a plate group residing in a zone of compression that will experience the most movement along the pressure direction, the stacked number of plates within such group is the lowest, each group being separated from adjacent groups by an inert, rigid spacer effective to transmit distortion-free pressure.

Stacking is defined herein to mean placement of predensified plates (or billets) directly on top of one another except for an intervening release agent such as ultra-thin graphite sheet, which is not rigid and cannot transmit distortion-free pressure.

Each of the plates or billets are preforms; a preform is defined herein to mean an agglomerated powder mixture having a density of 1.5–2.7 gm/cm$^3$ and is sufficiently rigid to handle and stack in a hot pressing assembly.

It is preferable if (a) the hot pressing is carried out with uniaxial pressure and the number of plates or billets in each of said groups proceeds from a maximum number of 5 to 3 to 2 to 1, the latter group has the lowest number and experiences the most relative movement; or (b) the hot pressing is applied biaxially and the sequence of groups contains the following numbers in order: 1, 2, 3, 10, 3, 2, 1 with the group having the single number experiencing the highest movement during compression and the group with the number 10 experiencing the lowest relative movement during compression. With respect to (a), this type of sequencing is appropriate for plates or billets having medium aspect ratios; for other aspect ratios, other types of sequencing would be more appropriate (see Sample 6).

Advantageously, the plates or billets are prepared by cold compacting a dry milled mixture of silicon powder, $Y_2O_3$, and $Al_2O_3$, and then heating the mixture in a nitrogen atmosphere for a period of time and at a temperature to agglomerate the mass to a density of about 2.3 gm/cm$^3$ and a chemical content of $\alpha$ and $\beta$ phase $Si_3N_4$, silicon yttrium oxynitrides, and some amorphous silicate. The cold compaction is carried out with a pressure of 1400–2000 psi.

The spacers are preferably fine grained, high density, high strength graphite with a thickness (0.25–1.5 inch) appropriate for withstanding the hot pressing forces and fully transmitting such forces comparable to a die wall. The thickness of the spacers is determined by the rule that in the zone of greatest axial movement for the body, the spacer associated therewith is the thickest because the forces encountered will be the greatest.

SUMMARY OF THE DRAWINGS

FIG. 2 is a view similar to that of FIG. 1 used in the environment of biaxial pressing; and FIG. 3 is a schematic illustration of a pressing assembly after densification which shows the disadvantages of using a stacking sequence not in conformity with this invention.

DETAILED DESCRIPTION

Figure 1:
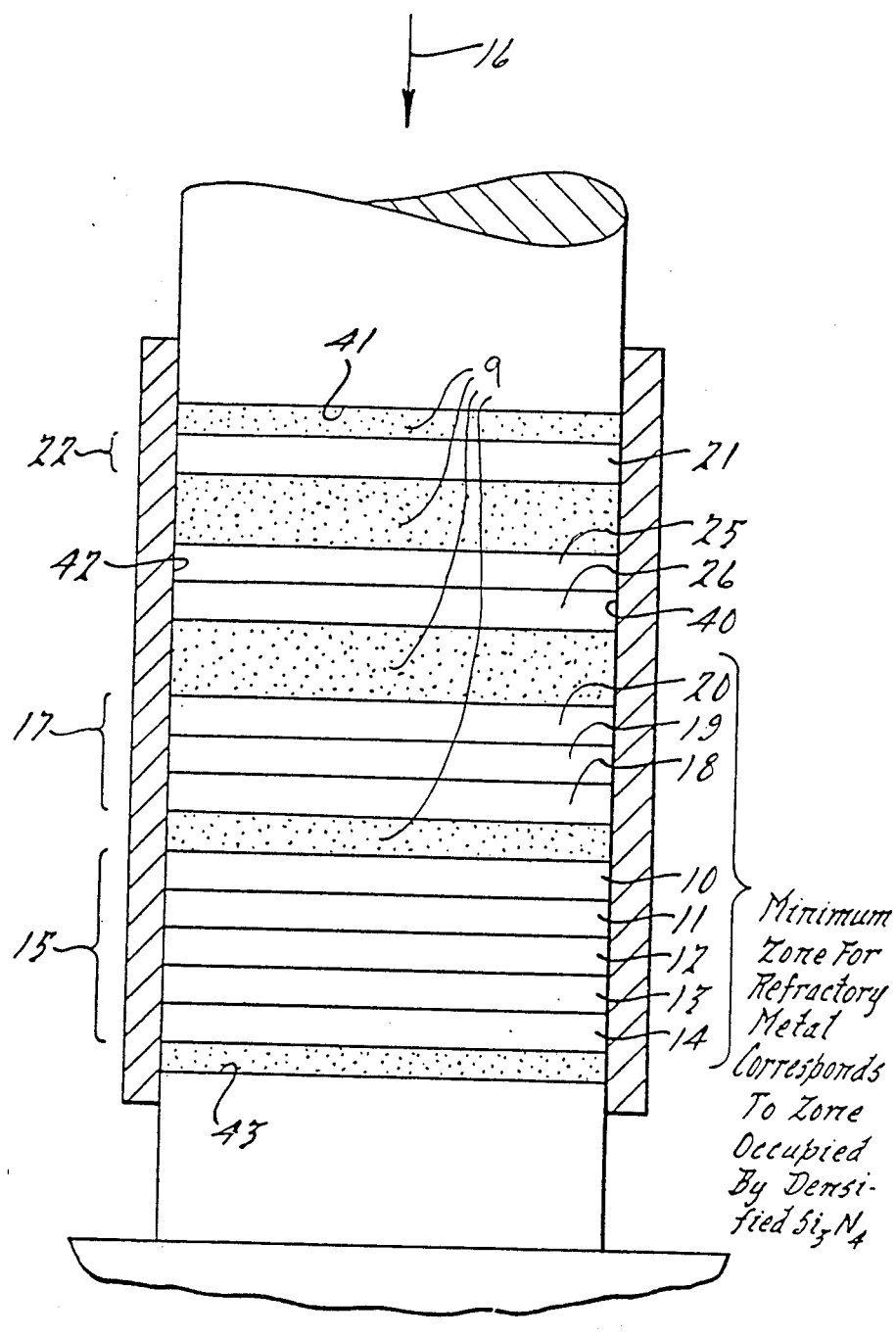
FIG. 1 is a schematic illustration in central sectional view of a pressing assembly showing the unique sequence of stacking in conformity with this invention for uniaxial pressure.

Certain physical problems are amplified when manufacturing economy is sought by the simultaneous production of a greater number of products, such as four or more plates or billets stacked and not separated by rigid spacers. Among these problems is severe distortion of the pressed product. Such distortion cannot be tolerated in the making of cutting tools from plates or billets. A plate or billet is defined herein to mean a predensified ceramic powder body having a certain aspect ratio (T/W) of 1:3 to 1:40 and a thickness in the range of 0.3–1.0 inch from which several useful cutting tools can be directly shaped by densifying and subdividing the plate by cutting through the thickness thereof.

A preferred method for making silicon nitride comprising objects with greater manufacturing economy and without distortion according to this invention is as follows.

1. Compacting

A compact is formed from a mixture of powdered silicon and reactive oxygen carrying powder agents. Reactive powder oxygen carrying agents are defined herein to mean powder ingredients that are effective to form second phase oxynitride crystallites, the appropriate silicates, when reacted with the silicon under a heated nitrogen atmosphere. The powder agents can be advantageously selected from the group consisting of $Y_2O_3$, $Al_2O_3$, $SiO_2$, $MgO$, $CeO_2$, $ZrO_2$, $HfO_2$, and rare earths. Use of selected quantities of $Y_2O_3$ and $Al_2O_3$ will result in the formation of a silicon yttrium oxynitride phase which (a) will uniformly be disbursed, and (b) displace the detrimental glassy silicate phase normally formed except for a controlled and limited amount of the latter. For purposes of the preferred method, a uniform powder mixture is prepared with 2000 grams of silicon powder (86.6% by weight of the mixture), 278 grams of $Y_2O_3$ (12% by weight of the mixture and 13.9% by weight of silicon powder), and 32 grams of $Al_2O_3$ (1.4% by weight of the mixture and 1.6% by weight of the silicon).

Silicon is selected to have 98% or greater purity and a starting average particle size of 8–9.2 microns. The major trace metal contaminants experienced with such impurity include iron, aluminum, calcium and manganese. Nonmetallic contaminants include carbon and $O_2$. The mixture is comminuted and blended by being charged into an inert milling jar along with grinding media in the form of cylinders, milled for 48 hours at 64 rpm, then the mixture is separated from the media. The resulting milled mixture will have an average particle size of 4 microns, the oxygen level after milling in air will be increased to 1.6% by weight of the silicon, and an oxide coating will be present on the silicon in an amount of 3.0% by weight. The ratio of the $Y_2O_3/SiO_2$ is controlled to be in the range of 1–7 and preferably about 4.

A measured quantity of the milled mixture is loaded into a cold pressed die arrangement and pressed at ambient conditions by use of 1400–1500 psi to form a round plate compact of a size about 6 inches in diameter and one-half inch in thickness, having a green density of 1.4 gm/cm$^3$.

2. Heating to Nitride

The plate is heated in a nitriding atmosphere to produce a silicon nitride comprising plate body having at least one dispersed silicon yttrium oxynitride phase, a silicate phase, and up to 0.5% by weight free silicon and unreacted oxygen carrying agents. The nitrided plate will have a size greater than the object to be subsequently formed and a density less than such object.

To carry out the nitriding, the plate compact is placed in an enclosed furnace, preferably evacuated to a pressure of less than 1 micron, and heated at a fast rate to 1200° F. (649° C.). The furnace is then filled with a gaseous mixture consisting of 72% by weight nitrogen, 3% hydrogen, and 25% helium at a pressure of about 2.7 psig. The total $O_2$ and $H_2O$ content in such gaseous mixture is less than 4 ppm. The temperature of the furnace is then increased to a nitriding temperature of 2000°–2500° F. (1093°–1427° C.) at a slower rate. Fresh nitrogen is continuously applied to the furnace to replace the nitrogen consumed in forming $Si_3N_4$ and silicon yttrium oxynitrides.

The nitrided body (billet) will preferably consist of silicon nitride (at least 60% of which is in the alpha form), silicon yttrium oxynitride in the $Y_1SiO_2N$ phase, and up to 0.5% of either unreacted silicon or yttria. This body is an intermediate product or commodity that has particular utility as a starting material for the hot pressing technique to follow. The nitrided plate has a thickness in the range of 0.3–1.0 inch and a width or diameter of 3–12 inches and a thickness/width ratio of 1:3 to 1:40 (aspect ratio). The billet density is in the range of 1.5–2.7 gm/cm$^3$.

3. Hot Pressing

The plates are stacked within a pressing assembly, the assembly having constraining side walls aligned with the direction of pressing to support the series of aligned plates normal to the direction of pressure. As shown in FIG. 1, the upper piston is used to apply uniaxial pressure to the stacked series of billets.

The pressing assembly has graphite walls 40-41-42-43. The walls and nitrided body are both coated with a slurry of boron nitride and dried. The graphite walls are additionally covered by graphite foil and/or molybdenum foil.

The sequence of stacking of the plates is critical to this invention. The plates are stacked in groups in progressively decreasing numbers so that for a plate group residing in a zone of compression that will experience the least movement along the pressure direction, the stacked number of plates is highest. For the plate group residing in a zone of compression that will experience the most movement along said pressure direction, the stacked number of plates is lowest. Each plate group is separated from adjacent plate groups by an inert, high density, rigid spacer 9 comprised of either graphite, boron nitride, or other inert pressure transmitting material. Preferably, the graphite spacers are covered with boron nitride which, in turn, is coated with graphite foil. The spacers maintain geometry, undergo no material transport, and are not affected by thermal pressure gradients. The thickness of the spacers is in the range of 0.25–1.5 inch and is determined by the rule that in the zone of greatest axial movement for the body, the spacer associated therewith is the thickest because of the greater forces encountered.

In particular, the stacking sequence of FIG. 1 shows that there are five plates, 10-11-12-13-14, placed in contiguous relationship with one another in the zone of movement 15 which is at the lowest portion of the stack, the latter experiencing the least amount of relative axial movement in the direction of compression 16.

The next plate group comprises three plates, 18-19-20, and will reside in an intermediate zone of movement 17 and, therefore, has a reduced number. The plate group containing the least number has plate 21 and is in the zone of highest movement 22. The plates fit directly on top of one another, except for a release agent film such as flexible graphite sheet (0.01 inch thick) which is not sufficiently rigid to transmit uniform pressure by itself.

Other combinations of plate groupings can be envisioned as long as the basic criteria of using decreasing numbers of plates in the plate groupings when progressing in a direction from the smallest amount of plate movement (plate 14) to the largest zone of plate movement (plate 21) is utilized.

In the environment of biaxial pressure, as shown in FIG. 2, the stacking sequence is as indicated. In the zone of least movement 23 there are 10 plates ($2\times 5$), in the zone of most movement 24 there is one plate. The stacking sequence is 1-2-3-10-3-2-1.

If the stacking sequence of this invention was not employed, the following phenomena would have resulted. As shown in FIG. 3, a pressure distribution is present which is brought about in part from side wall drag, that is, the edges of the plates 29-34 will contact the graphite side walls and impart a resistance to compression and promote a drag. The pressure gradient facilitates material transport from the outside diameter to the center of plates 30-31-32-33, and from the center to the outside diameter on plates 34, 35 and 36. These effects, upon cooling, yield "dished" hot pressed $Si_3N_4$ plates that require substantial reshaping by removal of material (diamond grinding) to produce a flat product.

The compression ratio for hot pressing is in the range of 1.2:1 to 2:1. The pressure is preferably applied in steps, about 150 psi at room temperature before heat-up. Pressure is then increased to 500 psi at 1800° F. (982° C.) and then the temperature is increased to 2400° F. (1371° C.) and pressure to 2500 psi, and finally the temperature is increased to 3000° F. (1649° C.) and pressure to 3700 psi. The latter conditions are maintained until full density is achieved. This usually requires 0.25–3 hours at the ultimate pressing temperature. The object is then cooled at any rate to room temperature.

The resulting object will consist essentially of beta phase silicon nitride, second phase crystallites in the form of silicon yttrium oxynitrides (predominantly $Y_1SiO_2N$) enveloped by amorphous silicate phase having a thickness of 4–10 angstroms and having no microporosity. The object preferably possesses a hardness of 89.0–91.0 on the 45-N scale, a density of 3.30–3.33 $gm/cm^3$, a fracture strength of greater than 85,000 psi at 1200° C. in a four-point bend test, and an oxidation resistance that prevents weight pickup by the object after 450 hours in air at 1000° C.

EXAMPLES

As shown in Table I, six examples were prepared to illustrate the importance of stacking sequence when hot pressing predensified ceramic plates in order to obtain high productivity and distortion-free plates at moderately low hot pressing compression ratios. Samples 1–6 were prepared generally in accordance with the preferred mode, wherein a mixture of Si, $Y_2O_3$, and $Al_2O_3$ was compacted and nitrided to form a silicon nitride plate having second phase crystallites. For Samples 1, 2 and 6, which represent a teaching of this invention, the nitrided plates with desired density were placed directly in the hot pressing assembly. For Samples 3 and 4, the plate was reground to form a powder, which loose powder was measured into the pressing assembly to assume a plate-like object conforming to the pressing cavity walls. Sample 3 is similar to the teachings of U.S. Pat. Nos. 3,632,708 and 3,535,132, while Samples 4 and 5 represent an attempt to increase productivity by stacking without sequencing groups.

The nitrided plates had the aspect ratios and densities specified in Table I. The sequencing of stacking was varied between the samples. Samples 1, 2, 4, 5 and 6 were true stackings since no rigid spacer was placed between plates, but Sample 3 was not stacked since only rigid spacers separated each of the plates. Samples 1, 2, 3 and 6 were divided into groups, while Samples 4 and 5 were not divided into groups. All were hot pressed in accordance with the preferred mode.

The results show that for Samples 1, 2 and 6, distortion-free plates were produced, productivity was very high with 20–22 plates in a given 10 inch usable hot zone pressing cavity, the density was as required, and the hot pressing only required a moderate hot pressing compression ratio of 1:4. Distortion-free is defined herein as the ability to remove no more than a thickness of 0.030 inch from each plate face and produce a flat plate. In contrast, Sample 3 did not use multiple plates within groups, no sequencing, and accordingly had very poor productivity within the given pressing cavity, even though distortion was limited. Samples 4 and 5 failed to use grouping of plates and had one very large, single group of plates. The deviation from flatness (distortion) was significantly excessive, causing some plates to have no utility and cause productivity to go down. Both Samples 3 and 4 required a very high hot pressing compression ratio due to the use of loose powder rather than predensified plates, which also detrimentally affected productivity.

plates to at least 95% of theoretical density with a compression ratio of 1.2:1 to 2:1.

2. The method as in claim 1, in which said hot pressing is carried out with uniaxial pressure and the number of plates in each of said groups proceeds from a maximum number of 5 to 3 to 2 to 1, the latter being for the group experiencing the most relative movement.

TABLE 1

| | Preform Conditions | | Stacking | | | | Hot Pressed Product | | | |
|---|---|---|---|---|---|---|---|---|---|---|
| Sample | Chemistry | Aspect ratio | Density gm/cm³ | Pressure application | # of plates in each group & sequence of groups | Separation between plates within each group (inches) | Thickness of spacer between groups (inches) | Density gm/cm³ | Deviation from flatness | # of plates in pressing cavity productivity | Compression ratio |
| 1 | Si₃N₄ + 2d phase crystallite | 1:16 | 2.3 | uniaxial | 9-5-3-2-1 | .01" non-rigid grafoil | .25-1.0 | 3.32 (99%+) | None | 20 | 1.4 |
| 2 | Si₃N₄ + 2d phase crystallite | " | " | biaxial | 1-2-3-10-3-2-1 | .01" non-rigid grafoil | .25-1.0 | 3.32 (99% +) | " | 22 | " |
| 3 | No preform (Si₃N₄ + 2d phase crystallites) | Loose powder 1:6 (6" diameter of die) | .8 | uniaxial | 1-1-1-1-1 | None | 1.0 | 3.25 | .02 | 5 | 4 |
| 4 | No preform (Si₃N₄ + 2d phase crystallites) | Loose powder 1:12 (6" diameter of die) | 1.5 | uniaxial | 15 | .01" non-rigid grafoil | None | 3.29 | Average is .68" | 15* | 2.2 |
| 5 | Si₃N₄ + 2d phase crystallites | 1:12 | 2.3 | uniaxial | 20 | .01" non-rigid grafoil | None | 3.32 | .73 | 20* | 1.4 |
| 6 | Si₃N₄ + 2d phase crystallites | " | " | uniaxial | 9-7-4-2 | .01" non-rigid grafoil | .5-1.5 | " | None | 22 | " |

*Distortion so severe on some plates that they could not be diamond ground into flat plates.

We claim:

1. A method of hot pressing ceramic plates in a pressing assembly having a constraining side wall aligned with the direction of pressing, comprising:
    (a) preparing a plurality of said plates, each having a thickness to width ratio in the range of 1:3 to 1:40 and a density in the range of 50–80% of full theoretical;
    (b) stacking a multiple number of said plates directly on top of one another within groups, except for the interposition of a compliant release coating between plates, and stacking a plurality of said groups with rigid force transmitting spacer plates therebetween into a pressure assembly in such a manner that the groups and spacer plates are stacked in an alignment along the direction of pressure to be applied and in contact with said contraining side wall, said groups having a progressively decreasing number of constituent plates so that for a group residing in a zone of pressing that will experience the least movement along said pressure direction the number of plates in the group is greatest and for a group residing in a zone of pressing that will experience the most movement along said pressure direction the number of plates in the group is the smallest; and
    (c) hot pressing said stacked groups of plates under pressure and temperature to densify each of said 3. The method as in claim 1, in which said pressure is applied biaxially and the sequence of groups contains the following numbers in order: 1, 2, 3, 10, 3, 2, 1, with the group having the single number experiencing the highest movement during compression and the group with the number 10 experiencing the lowest movement during compression.

4. A method of making a plurality of dimensionally accurate hot pressed silicon nitride plates, comprising:
    (a) preparing a plurality of silicon nitride comprising plates having a thickness to width ratio in the range of 1:3 to 1:40 and a density of 1.5–2.7 gm/cm³;
    (b) stacking said plates into a pressure assembly having walls to support said plates normal to the direction of pressure, said stacking being in groups of progressively decreasing number so that for a plate group residing in a zone of said pressing that will experience the least movement along said pressure direction the stacked number of the plates is greatest within said group and for a plate group residing in a zone of pressing that will experience the most movement along said pressure direction the stacked number of plates within said group is the lowest, each group being separated from adjacent groups by an inert rigid spacer; and (c) hot pressing said stacked plate groups under pressure and temperature to densify each of said plates to at least 95% of theoretical density with a pressing ratio of 1.2:1 to 2:1.

5. The method as in claim 4, in which said hot pressing is carried out with uniaxial pressure and the number of plates in each of said groups proceeds from a maximum number of 5 to 3 to 2 to 1, the latter being for the group experiencing the most relative movement.

6. The method as in claim 4, in which said pressure is applied biaxially and the sequence of groups contains the following numbers in order: 1, 2, 3, 10, 3, 2, 1, with the group having the single number experiencing the highest movement during compression and the group with the number 10 experiencing the lowest movement during compression.

7. The method as in claim 4, in which said plates are prepared by heating a mixture of silicon powder, $Y_2O_3$, and $Al_2O_3$ in a nitrogen atmosphere for a period of time and at a temperature to agglomerate said mass to a density of about 2.3 $gm/cm^3$ and a chemical content comprised substantially of alpha phase silicon nitride and silicon yttrium oxynitrides.

8. The method as in claim 4, in which said hot pressing is carried out in increments by applying about 150 psi at room temperature, heating to 1800° C. accompanied by 500 psi pressure, then heating further to 2400° F. with 2500 psi pressure, and finally to 3000° F. with 3700 psi pressure.

9. The method as in claim 4, in which said plates are prepared by cold compacting a dry ball milled mixture of silicon, $Y_2O_3$, and $Al_2O_3$ powder and then heating in a nitrogen atmosphere to convert said mixture to substantially silicon nitride and silicon yttrium oxynitrides, said cold compaction being carried out with a pressure of about 1400–1500 psi.

10. The method as in claim 4, in which each inert rigid spacer has a thickness of 0.25–1.5 inch.

11. The method as in claim 10, in which the thickness of said inert rigid spacer varies with the total overall thickness of the plate group immediately adjacent the inert spacer, said thickness being determined by the rule that in the zone of greatest axial movement for the plate, the spacer associated therewith is the thickest.

* * * * *